United States Patent [19]

Harris

[11] Patent Number: 4,882,449

[45] Date of Patent: Nov. 21, 1989

[54] CALIXARENE DERIVATIVES, AND USE OF SUCH COMPOUNDS FOR SEQUESTRATION OF METALS

[75] Inventor: Stephen J. Harris, Dublin, Ireland

[73] Assignee: Loctite Corporation, Newington, Conn.

[21] Appl. No.: 20,918

[22] Filed: Mar. 2, 1987

Related U.S. Application Data

[63] Continuation-in-part of Ser. No. 870,677, Jun. 4, 1986, Pat. No. 4,699,966, and a continuation-in-part of Ser. No. 825,012, Jan. 31, 1986, Pat. No. 4,695,615, which is a continuation of Ser. No. 717,251, Mar. 28, 1985, Pat. No. 4,642,362.

[30] Foreign Application Priority Data

Mar. 7, 1986 [IE] Ireland .................................. 596/86
Aug. 29, 1986 [IE] Ireland ................................ 2319/86

[51] Int. Cl.$^4$ ............................................. C07F 7/10
[52] U.S. Cl. .................................... 556/419; 568/325; 568/631; 568/632; 568/633; 560/75
[58] Field of Search .......................... 556/419; 560/75; 568/325, 631, 632, 633

[56] References Cited

U.S. PATENT DOCUMENTS 4,556,700 12/1985 Harris et al. ......................... 526/245
4,642,362 2/1987 Harris et al. ......................... 556/419
4,699,966 10/1987 Harris et al. ......................... 528/33

Primary Examiner—Ronald W. Griffin
Attorney, Agent, or Firm—Edward K. Welch, II; Eugene F. Miller

[57] ABSTRACT

Novel nitrogen-containing calixarene derivatives which are useful for sequestration of transition metals are represented by the formulae

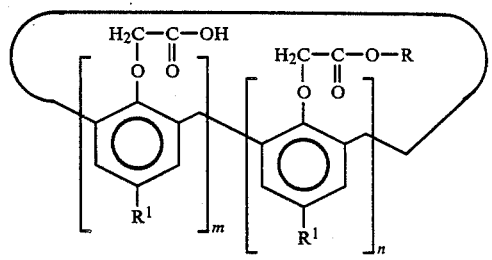

and

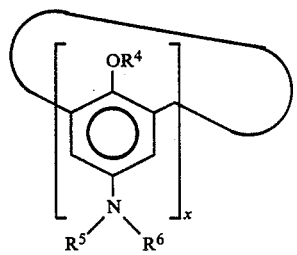

wherein
m+n=4,6 or 8
n=an integer 1–8
m=an integer 0–7
x=4, 6 or 8
$R^1$ is H, alkyl, aralkyl, alkoxy, aroyl, or alkoyl,
R is aliphatic or aromatic, unsubstituted or substituted hydrocarbyl containing nitrogen,
$R^4$ is unsubstituted or substituted hydrocarbyl, carbonyl or aryl;
$R^5$ and $R^6$ (which may be the same or different) are hydrogen, or unsubstituted or substituted hydrocarbyl.

A process for separating transition metals from mixtures containing such metals comprises treating such a mixture with a calixarene derivative of formula I or II as defined above and separating therefrom a complex of the calixarene derivative and the transition metal. The complex may then be broken down, the transition metal recovered and the calixarene derivative recycled for further use in the process.

A linear or crosslinked polythioether comprises the addition reaction product of a compound having at least two thiol groups per molecule and a calixarene derivative of formula II above wherein R is alkenyl or alkynyl.

11 Claims, No Drawings

CALIXARENE DERIVATIVES, AND USE OF SUCH COMPOUNDS FOR SEQUESTRATION OF METALS

This application is a continuation-in-part of U.S. Ser. No. 870,677, filed June 4, 1986, now U.S. Pat. No. 4,699,966, which is a continuation-in-part of U.S. Ser. No. 717,251, filed Mar. 28, 1985, now U.S. Pat. No. 4,642,362. This application is also a continuation-in-part of U.S. Ser. No. 825,012, filed Jan. 31, 1986, now U.S. Pat. No. 4,695,615, which is a continuation-in-part of U.S. Ser. No. 717,251, filed Mar. 28, 1985, now U.S. Pat. 4,642,362.

BACKGROUND OF THE INVENTION

1. Field of the Invention

This invention relates to novel calixarene derivatives and to the use of such derivatives for sequestration of metals, particularly transition metals including precious metals. The invention also concerns a process for selectively sequestering transition metals from aqueous mixtures of alkali metals and transition metals, as well as a process for regenerating the calixarene derivative from its complex with the transition metal.

2. Description of Related Art.

U.S. Pat. No. 4,556,700 Harris et al describes the use in adhesive compositions of calixarene compounds represented by the forumla

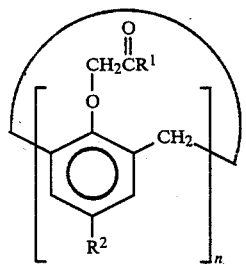

where $R^1$ is alkyl, alkoxy, substituted alkyl or substituted alkoxy; $R^2$ is H or alkyl; and n=4, 6 or 8.

McKervey et al., J. Chem. Soc. Commun. 1985 p. 388 describes the cation transfer properties of Alkyl Calixaryl acetates. These ester calixarenes are only capable of sequestering alkali metals or alkali metals together with transition metals.

Olmstead et al., J. Am. Chem. Soc., 1985, 107, 8087–8091, describe complexes of p-tert.-Butylcalix[4]arene with the transition metals Titanium (IV), Iron (III) and Cobalt (II).

Izatt et al, J. Am. Chem. Soc., 1985, 107, 63–66 describe cation transport from multiple alkali metal cation mixtures using a liquid membrane system containing a series of calixarene carriers, specifically p-tert.-butylcalix[4]arene, -calix[6]arene, and -calix[8]arene and p.-tert.-pentylcalix[4]arene, -calix[6]arene and -calix[8]arene.

Yokota et al, Makromol, Chem., Rapid Commun., 5, 767–770 (1984) describe polymers with thiacrown ether units which are more effective in binding metal ions such as $Cu^{2+}$, $Ni^{2+}$, $CO^{2+}$ and $Hg^{2+}$ than in binding alkali metal ions.

Kimura et al., J. Chem. Soc., Chem. Commun., 1985, 1041 describe a macrocyclic dioxotetra-amine which acts as a carrier for the membrane transport of $CU^{2+}$ ions.

Izatt et al., J. Am.Chem. Soc., 1983, 105, 1785–1790 describe macrocyclic ligand carriers which showed transport selectively for $Ag^+$—$M^{n+}$ binary cation mixtures in a $H_2O$—$CHCl_3$—$H_2O$ liquid membrane system. Selection of macrocycles having appropriate combinations of oxygen with either nitrogen, or sulfur donor atoms led to selective transport of $Ag^+$ in preference to any of the other cations studied.

SUMMARY OF THE INVENTION

The present inventor has now prepared novel nitrogen-containing calixarene derivatives which surprisingly have the capability of sequestering transition metals selectively but not sequestering alkali metals.

The present invention provides novel nitrogen-containing calixarene derivatives selected from the group represented by the formulae:

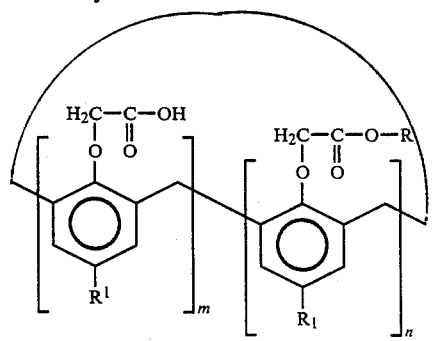

and

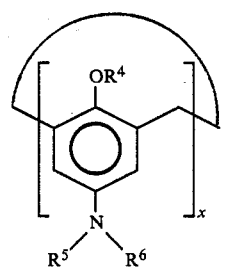

wherein
m+n=4, 6, or 8
n=an integer 1-8
m=an integer 0-7
x=4, 6 or 8
$R^1$ is H, aralkyl, alkoxy aroyl, or alkoyl,
R is aliphatic or aromatic, unsubstituted or substituted, hydrocarbyl containing nitrogen.
$R^4$ is unsubstituted or substituted hydrocarbyl, carbonyl or aryl;
$R^5$ and $R^6$ (which may be the same or different) are hydrogen, or unsubstituted or substituted hydrocarbyl.

In the derivatives of formula I, when m and n are greater than 1, the m aryl groups having the —OCH$_2$—C(O)OH side chain may be interspersed around the ring between the n aryl groups having the —OCH$_2$C(O)OR side chain.

Preferably n is greater than or equal to ½(m+n).

The invention also provides a process for separating transition metals from mixtures containing such metals which comprises treating such a mixture with a calixarene derivative of formula I or II as defined above and separating therefrom a complex of the calixarene derivative and the transition metal. Normally, the process also includes breaking down the complex, recovering the transition metal, and recycling the calixarene derivative for further use in the process. The process is particularly applicable to the separation of transition metals from aqueous mixtures of such metals with alkali metals and it is especially useful for the recovery of precious metals.

In the calixarene derivative for Formula I, radical R contains nitrogen which may or may not form part of a heterocyclic ring. The radical R may suitably contain an amino or amide group, in particular, R may be a group of the formula

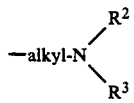   III where $R^2$ and $R^3$ represent H or substituted or unsubstituted hydrocarbyl, especially alkyl.

Alternatively, the radical R may contain a heterocyclic ring which may be saturated or unsaturated, aliphatic or aromatic, for example a 5- or 6-membered ring containing a nitrogen atom such as pyridine, pyrimidine, piperidine, pyrrole, pyrrolidine, or containing 2 nitrogen atoms such as imidazole or pyrazole, or for example a fused ring such as benzimidazole, purine, quinoline, isoquinoline or carbazole. In particular, R may be a radical of the formula

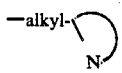   IV where 
represents a heterocyclic ring of the kind described above.

In another alternative, R may be aromatic compound of the formula

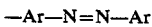   V or an azo compound of the formula $-Ar-N=N-Ar$   VI where Ar represents an aromatic radical.

In a further alternative, which is less preferred, the radical R may contain a nitrogen atom which forms an oxime group with the oxygen atom of the acid side chain of the calixarene derivative, i.e. R may be of the formula

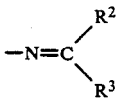   VII where $R^2$ and $R^3$ are as defined above.

In all of the above formulae, hydrocarbyl is preferably alkyl or alkenyl; alkyl or alkenyl preferably have 1-10 carbon atoms, more particularly 1-5 carbons atoms. If R, $R^4$, $R^5$ or $R^6$ is substituted it may suitably be substituted with one or more halo, oxo or nitro groups.

$R^1$ is preferably H or lower alkyl having 1-5 carbon atoms, particularly tert.butyl.

Compounds of formula II wherein $R^4$ is an ethylenically or acetylenically unsaturated group can be polymer bound by thiol-ene addition reactions as described in U.S. patent application Ser. No. 717,251 Harris et al (European Patent Application No. 86302342.0 Loctite (Ireland) Limited).

The invention therefore also provides a linear or cross linked polythioether comprising the addition reaction product of a compound having at least two thiol groups per molecule and a calixarene derivative of formula II wherein $R^4$ is alkenyl or alkynyl.

A polymer-bound calixarene derivative may be recovered from a reaction mixture more easily than the calixarene derivative alone. For example a polymer-bound calixarene derivative according to the invention, which retains the metal-sequestering capability of the unbound calixarene derivative, may be used to solubilise copper II benzoate in ε-caprolactone which together with diphenyl iodonium hexafluoroarsenate and benzoin forms a diaryliodonium-redox catalyst system for its conversion to polycaprolactone (see U.S. Pat. No. 4,192,924 by J. Crivello, General Electric Co., Mar. 11, 1980). Crosslinked polymer bound calixarene derivative may be easily recovered by virtue of its insolubility in organic solvents and be reused (after appropriate treatment if necessary).

Calixarene compounds may be readily synthesised by methods described in C.Gutsche, Acc.Chem. Res., 16, 161-170(1983), and references cited therein, as well as in U.S. Pat. No. 4,556,700, Harris et al, the disclosures of which are incorporated herein by reference.

DESCRIPTION OF THE PREFERRED EMBODIMENTS

The invention may be further understood with reference to the following non-limiting examples.

Preparation of Tetramer Starting Materials A & B

Preparation of

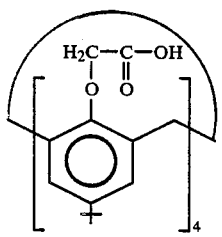   A 34.0g tetraethylacetate of p-t-butyl calix-4-arene (0.034 mole) (prepared as in U.S. Pat. No. 4,556,700 Harris et al) was refluxed for 72 hours with 76.0 g KOH (1.35 mole), 70 mls IMS and 70 mls water. The reaction mixture was then added to 200 mls 35% aqueous HCl and the white solid was filtered and washed several times with water to remove acid and then dried to give 26.0 g of product characterised by i.r. spectroscopy as title compound A Preparation of

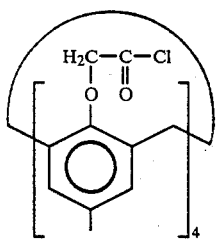

To 4.4 g (0.005 mole) of the acid derivative prepared above in 91 mls dry dichloromethane was added 21.6g oxalyl chloride with stirring under nitrogen at room temperature dropwise during 30 minutes. After several hours the white suspension had completely dissolved giving a clear pale yellow liquid which was left stirring at room temperature overnight. After removal of volatiles 4.77g colourless solid was left identified by i.r. spectroscopy as the acid chloride B which was not further purified in view of its moisture sensitivity.

EXAMPLE 1

Preparation of

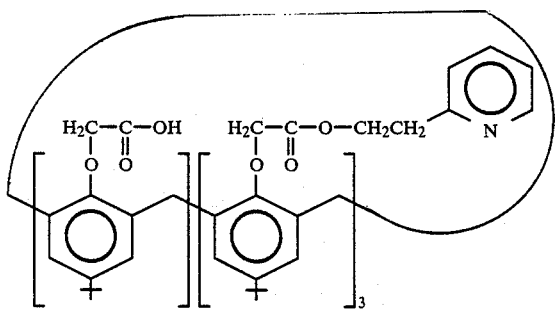

To 3.08g of the acid chloride Starting Material B (0.0032 mole) in 20 mls NaH dried THF (tetrahydrofuran) at 0° C. was added dropwise 2.04g (0.026 mole) dry pyridine and 3.18g (0.026 mole) 2-pyridineethanol under nitrogen with stirring during 15 minutes. A white precipitate formed and the stirred reaction mixture was allowed to warm to room temperature and left stirring 72 hours. The reaction mixture was then poured into 100 mls ice water and then extracted with dichloromethane which was washed well twice with water then dried over magnesium sulphate to give after removal of volatiles 2.4 g crude white product. This material was chromatographed on neutral alumina using dichloromethane as eluent to give after removal of solvent high purity colourless crystalline product mpt. 66°–7° C. characterised by i.r. spectroscopy and elemental analysis as title compound.

i.r. spectroscopy results: $\nu$ 1750(S)cm$^{-1}$—C═O.

Elemental Analysis results: (Calc'd for $C_{73}H_{85}O_{12}N_3$ C:73.28, H:7.16, O 16.05, N:3.51; Found, C:72.98, H:7.19, O :16.45, N:3.41)

EXAMPLE 2

Preparation of

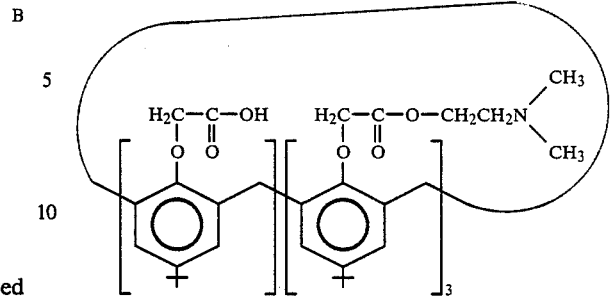

To 4.78 g (0.005 mole) of the acid chloride Starting Material B in 50 mls NaH dried THF at 0° C. was added dropwise 3.2 g (0.040 mole) dried pyridine, 3.6 g (0.040 mole) 2-dimethylaminoethanol and 10 mls dry THF under nitrogen with stirring during 25 minutes. The stirred reaction mixture was allowed to reach room temperature then allowed to stir for a further 48 hours. After this time all volatiles were removed under vacuum and the white solid added to water and the solid filtered off was washed well again with water and dried at 55° C. to give 4.02 g white crude product. This material was chromatographed on neutral alumina using dichloromethane as eluent to give after removal of solvent colourless crystalline product m.pt. 36°–7° C. characterised by i.r. spectroscopy and elemental analysis as title compound.

i.r. Spectroscopy results : $\nu$1750(S)cm$^{-1}$—C═O

ELemental Analysis results: (Calc'd for $C_{64}H_{91}O_{12}N_3$ C:70.23, H:8.38, N:3.84; Found C:69.47, H:8.78, N:4.01)

EXAMPLE 3

Preparation of

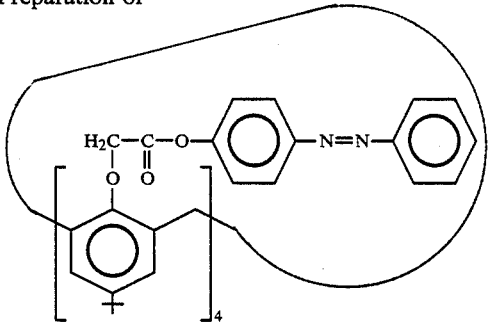

To 3.08 g (0.0032 mole) of the acid chloride Starting Material B in 20 mls NaH dried THF at 0° C. was added dropwise 2.04 g (0.026 mole) dry pyridine, 3.07 g p-hydroxyazobenzene (0.0155 mole) in 5 mls dry THF under nitrogen with stirring during 15 minutes. The reaction mixture was then allowed to reach room temperature with stirring and then left stirring a further 72 hours after which the reaction mixture was poured into 100 mls 5% aqueous HCl and the orange precipitate resulting washed well with 5% aqueous HCl and then with water and dried under vacuum to give 1.6 g crude product. Chromatography on neutral alumina with dichloromethane as eluent afforded high purity orange crystalline product m.pt. 110°–112° C. characterised by i.r. spectroscopy and elemental analysis as title compound.

i.r. Spectroscopy results: $\nu$ 1760(S)cm$^{-1}$—C═O

Experimental Analysis results: (Calc'd for $C_{100}H_{96}O_{12}N_8$ C:74.98, H:6.04, O: 11.99, N:7.00; Found C:74.76, H:6.14, O 11.52, N:6.52.

EXAMPLE 4

Preparation of

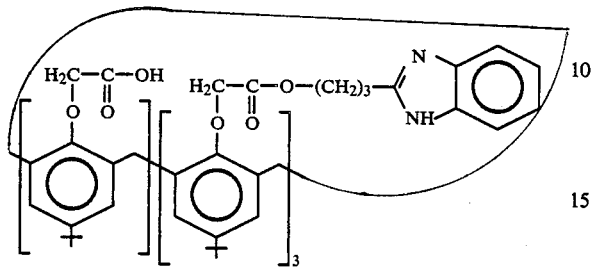

To 3.08 g (0.0032 mole) of the acid chloride Starting Material B is 35 mls dry N-methylpyrrolidone at 0° C. was added dropwise 2.04 g (0.026 mole) dry pyridine and 2.73 g (0.0155 mole) 2-(3-hydroxypropyl)benzimidazole in 5 mls dry N-methylpyrrolidone under nitrogen with stirring during 15 minutes. The stirred reaction mixture was allowed to warm to room temperature and left stirring a further 72 hours. The reaction mixture was then poured into 100 mls 5% aqueous HCl and the buff coloured precipitate washed well with 5% aqueous HCl then water then dried under vacuum to give 2.4 g crude product as a buff coloured solid. Chromatography on neutral alumina using dichloromethane as eluent afforded high purity off-white crystalline product m.pt. 141°-3° C. characterised by i.r. spectroscopy and elemental analysis as title compound.

i.r. Spectroscopy results: $\nu$ 1750(S)cm$^{-1}$—C=O.

Experimental Analysis results: (Calc'd for $C_{82}H_{94}O_{12}N_6$ C:72.65, H:6.99, N:6.20; Found C:70.43, H:6.91, N:6.14; the carbon analysis is low due to the low volatility of high molecular weight material.

EXAMPLE 5

Preparation of

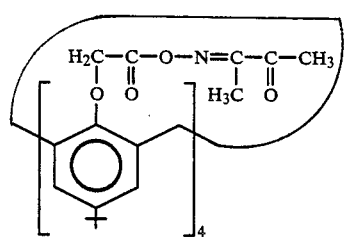

To 2.6 g (0.0027 mole) of the acid chloride Starting Material B in 20 mls NaH dried THF of 0° C. was added dropwise 2.2 g (0.022 mole) 2,3-butanedione monoxime and 1.7 g (0.021 mole) dry pyridine under nitrogen with stirring during 15 minutes. The stirred reaction mixture was allowed to warm to room temperature and left stirring for 72 hours. The reaction mixture was then poured into 5% aqueous HCl to give an off-white solid which was taken up into dichloromethane which was then washed again with 5% aqueous HCl and three times with water (to remove 2,3-butanedione oxime staring materal) then dried with magnesium sulphate. Removal of volatiles gave 1.9 g high purity off-white crystalline product m.pt. 100°-103° C. characterised by i.r. spectroscopy and elemental analysis as title compound.

i.r. Spectroscopy results: $\nu$ 1785(S)cm$^{-1}$C=O, 1700(S)cm$^{-1}$C=O.

Elemental Analysis results: (Calc'd for $C_{68}H_{84}O_{16}N_4$ C:67.31, H:6.98, O:21.10, N:4.62; Found C:66.96, H:6.96, O:21.28, N:4.52)

Preparation of Octamer Starting Materials C & D.
Preparation of

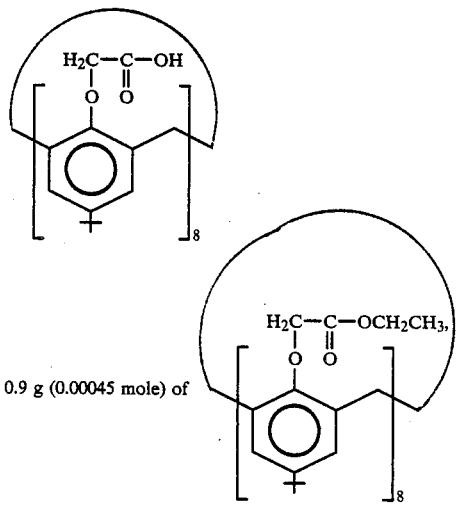

0.9 g (0.00045 mole) of (prepared by following the procedure of U.S. Pat. No. 4,556,700 Harris et al) and 2.1 g (0.037 mole) potassium hydroxide, were refluxed together in 4 mls IMS (or absolute ethanol) and 4 mls water for 48 hours. After this period of time the reaction mixture was poured into excess 10% aqueous HCl and the white precipitate washed with water and dried to give 0.74 g Starting Material C (93% yield) whose infra red spectrum was consistent with the above structure.

Prepartion of

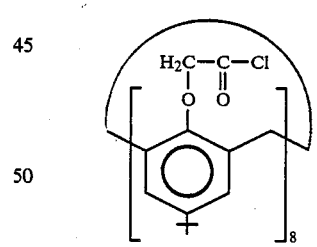

0.74 g (0.00042 mole) of the acid derivative C was stirred with 3.6 g (0.028 mole), oxalyl chloride, in 14.5 mls dichloromethane under nitrogen at room temperature for 48 hours. After this period of time all the volatiles were removed from the clear solution including the excess oxalyl chloride under vacuum to give 0.8 g Starting Material D (ca 100% yield) whose infra red spectrum was consistent with the structure above.

It was not further purified in view of its moisture sensititvity i.r. spectroscopy results: 1800(S)cm$^{-1}$—C=O.

EXAMPLE 6

Preparation of

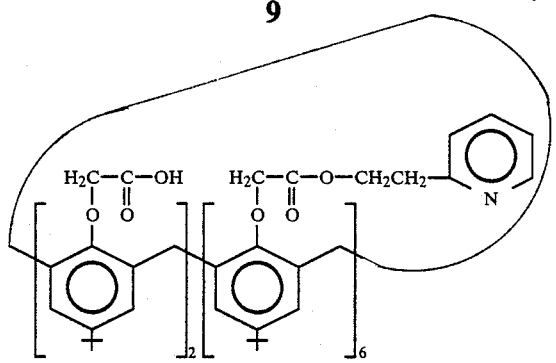

0.8 g (0.00042 mole) of the acid chloride Starting Material D in 2mls dried THF was added dropwise to 0.83 g (0.0067 mole) 2-(2-hydroxyethyl) pyridine and 0.53 (0.0067 mole) pyridine in 10 mls dried THF at 0° C. during 10 minutes under nitrogen. The reaction mixture was then allowed to stir a further 2 hours at 0° C. then 72 hrs. at room temperature. After this time all volatiles were removed and the residual solid washed well with water and dried to give 0.8 g crude title compound whose infra red spectrum was consistent with the above structure. It was purified by elution through neutral alumina using dichloromethane as eluent. m.pt. 150° C. (decomposition).

i.r. Spectroscopy results: $\nu$ 1750(S)cm$^{-1}$—C=O

Elemental Analysis results: (Calc'd for $C_{146}H_{170}O_{24}N_6$, C:73.28, H:7.16, N:3.51, Found C:69.51, H:7.09, N:3.64; the carbon analysis is low due to low volatility of high molecular weight materials).

EXAMPLE 7

Allyl ether of p-Aminocalix-4-arene (a) Preparation of p-Nitrocalix-4-arene

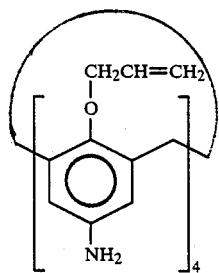

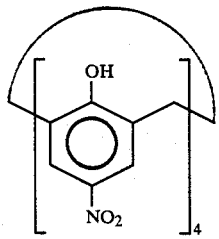

p-Nitrocalix-4-arene was prepared in high yield following the method of S. Shinkai et al Tetrahedron Letters 26 (28) P3343–4 1985 which was used by these workers for the preparation of p-nitrocalix-6-arene. Thus 5.0g (0.0077 mole) calix-4-arene was heated in 50 ml concentrated sulphuric acid for 17 hrs at 95° C. After cooling the reaction mixture was diluted with 90 mls cold water and then treated with 4.9g 69% $HNO_3$ for 17 hrs at 0°-5° C. When the reaction mixture was diluted with water a fine buff coloured precipitate formed which was centrifuged and washed several times with water, then dried in the air to give 6.3g p-nitrocalix-4-arene.

i.r. spectroscopy results :$\nu$ 3400 (m,broad) OH, 1335(s) cm$^{-1}$ $NO_2$. HPLC (High pressure liquid chromatography 100A+500A+1000A Columns Waters Millipore Sugar Analyser liquid Chromatograph) of fully silylated derivative in dichloromethane, elution volume 14.3 minutes single sharp peak 1.5 mls/minute.

(b) Preparation of Allyl ether of p-nitrocalix-4-arene 1.37g (0.002266 mole) p-nitrocalix-4-arene prepared as in 7a above was refluxed in 50 mls sodium hydride dried THF with 13.7g (0.113 mole) allyl bromide and 2.18 g (0.091 mole) sodium hydride under nitrogen with stirring for 72 hours. After this time several mls of water were added to the reaction mixture to destroy the excess sodium hydride and the THF was removed with a rotary evaporator; the residue was taken up in more water and washed to give 1.70g of yellow product. This material was chromatographed on neutral alumina using dichloromethane as eluent to give after removal of solvent pale yellow high purity powder (m.pt. 67°-67.5° C.) characterised by i.r. spectroscopy and elemental analysis as

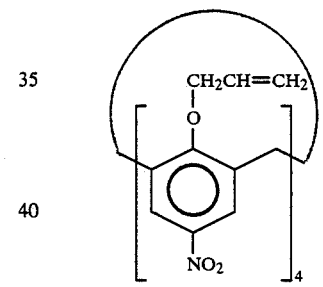

i.r. spectroscopy results=$\nu$ 1600(w) 1500(w) cm$^{-1}$ $H_2C$=CH (no 3400 cm$^{-1}$ due to OH).

Elemental Analysis results : (Calc'd for $C_{40}H_{36}O_{12}N_4$ C:62.82, H:4.75, N:7.33, O: 25.11;

Found C:63.24, H:5.15, N:6.93, O; 25.37).

(c) Preparation of Allyl either of p-Aminocalix-4-arene

To 0.150g (0.000196 mole) of the allyl ether of p-nitrocalix-4-arene was added 0.0785 g (0.00157 mole) hydrazine hydrate and 0.24g graphite and 1 ml absolute ethanol and the entire was refluxed overnight under nitrogen. The reaction mixture was then filtered and the solid washed with ethanol and the volatiles removed from the combined filtrates under vacuum at room temperature to give 0.104g of pale yellow powdery solid. This material was chromatographed on neutral alumina using dichloromethane as eluent to give after removal of solvent high purity colourless solid product (m.pt. 87°-88° C.) which was characterised by i.r. spectroscopy and elemental analysis as

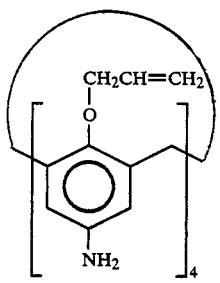

i.r. spectroscopy results : $\nu$ 3320(m) cm$^{-1}$ NH (stretch) 1590 (s) cm$^{-1}$ NH (bend)

Elemental analysis results=(Calc'd for C$_{40}$H$_{44}$N$_4$O$_4$ C: 74:50, H: 6.88, N: 8.69, 0: 9.93;

Found, C: 73.98, H: 7.30, N: 8.19, 0: 10.42)

The procedure followed above for the conversion of nitro calixarene to the aminocalixarene was as described in "Graphite-catalysed Reduction of Aromatic and Aliphatic Nitro Compounds with Hydrazine Hydrate" by B. H. Han et al Tetrahedron Letters 26(50) p 6233-4 1985.

EXAMPLE 8

Reaction Calixarene with Polythioether

The procedure followed was as described in Example 13 of U.S. patent application Ser. No. 717,251 Harris et al, (European Patent Application No. 86302342.0 Loctite (Ireland) Limited).

A formulation was prepared consisting of 0.060 g of the allyl ether of p-Aminocalix-4-arene prepared as in Example 7c and 1.44 g of a solution prepared from 0.603 g of pentaerythritol tetrakis ($\beta$-mercapto-propionate), 0.035 g 2,2-dimethoxy-2-phenyl acetophenone, 8.94 g of toluene and 9.56 g chloroform. This solution was applied to a glass plate which was irradiated under a medium pressure Mercury arc at an intensity of 55 mw/cm$^2$ at 365nm for 120 seconds followed by a post bake at 90° C. for one hour to remove residual solvents.

The formulation had cured to a yellow brittle film which was insoluble in acetone, attesting to it being a crosslinked polymer. The original individual components were all acetone soluble.

Ion extraction by Nitrogen-Containing Calixarenes.

The ion binding abilities of nitrogen-containing calixarenes were measured by extraction of metal picrate from aqueous into organic madia. In each experiment a solution of the nitrogen-containing calixarene in dichloromethane was prepared at $2.5 \times 10^{-4}$M. Silver, cupric, and ferric picrates were prepared as aqueous $2.5 \times 10^{-4}$M solutions (see Aggarwal et al Def. Sci.J., Vol. 25, October 1975, 153). A solution of picric acid in 0.1 M aqueous sodium hydroxide was prepared such that the concentration of sodium picrate was $2.5 \times 10^{-4}$M. Equal volumes of each solution (5 millilitres) were shaken together for 3 minutes and the percentage extraction of metal picrate into organic phase was determined by measuring the increase in absorbance of dichloromethane layer at $\lambda$m ca 355 nm(cupric, ferric, silver picrate) and $\lambda$m 387 nm (sodium picrate) in a u.v. spectrophotometer. The results are presented in the following table. Also included in the table are extraction data for 18-crown-6, 2,3-butanedione monoxime, bezimidazole and ethylacetate p-t-butylcalix-4-arene as comparison data -

| Compound | m.p. | Silver Picrate | Cupric Picrate | % $\epsilon$ Ferric Picrate | Basic Sodium Picrate |
|---|---|---|---|---|---|
| Ex. 1 | 66-7° C. | 77.0 | 11.4 | 44.7 | 0.0 |
| Ex. 4 | 141-3° C. | 93.3 | 70.2 | 94.7 | 0.0 |
| Ex. 2 | 36-7° C. | 26.3 | 38.8 | 40.7 | 0.0 |
| Ex. 3 | 110-2° C. | 25.6 | 23.3 | 30.6 | 0.0 |
| Ex. 6 | 150° C.(d) | 80.4 | 32.8 | — | 0.0 |
| Ex. 5 | 100-3° C. | 0.0 | 3.4 | 9.4 | 1.0 |
| Ex. 7 | 87-8° C. | 44.3 | 18.8 | — | 0.0 |
| Benzimidazole | | 1.1 | 0.9 | 1.7 | — |
| 2,3-butadione monoxime | | 1.5 | 0.0 | 1.1 | — |
| 18-crown-6 | | 2.7 | 1.0 | 3.0 | 13.5 |
| EABCA* | 154-6° C. | 17.9 | 4.2 | 12.1 | 94.6 |

*ethyl-acetate p-t-butyl calix-4-arene
(d) = decomposes

The ability of these nitrogen-containing calixarenes to selectively sequester certain metals from mixtures of metal picrates was demonstrated in the following way.

A $2.5 \times 10^{-4}$M dichloromethane solution of the compound of Example 2 was shaken for 10 minutes with an equal volume of $2.5 \times 10^{-4}$M aqueous sodium picrate (pH7), $2.2 \times 10^{-4}$M cupric picrate mixture.

The $\lambda$m 355 nm of the dichloromethane layer at this point after shaking was 2.29 absorbance indicating spectrophotometrically a 38.9% uptake of cupric picrate. The aqueous layer was analysed by atomic absorption for sodium and copper before and after shaking with calixarene solution and dichloromethane blank and the following results were obtained viz:

| Aqueous Sample Cupric Picrate/ Sodium Picrate mixture | Cu ppm | Na ppm |
|---|---|---|
| Before shaking with Calixarene Solution | 12 | 6 |
| Shaking with Dichloromethane alone as a Control | 12 | 7 |
| After Shaking with the dichloromethane solution of the compound of Example 2 | 6 (50%) | 6 |

As can be clearly seen the calixarene derivative is capable of specifically sequestering copper from a cupric picrate/sodium picrate aqueous mixture and this phenomenon has thus now been verified both spectrophotometrically and by atomic absorption analysis.

Regeneration of Calixarene From Its Silver Metal Complex.

That the calixarene could be regenerated and made to give up its sequestered metal and thence be reutilised was demonstrated by the following two experiments carried out on an aqueous silver picrate/sodium picrate mixture on which atomic absorption analysis had been carried out.

Equal volumes of $2.5 \times 10^{-4}$M aqueous silver picrate, $2.5 \times 10^{-4}$M aqueous sodium picrate mixture and $8.3 \times 10^{-5}$M of the compound of Example 1 in dichloromethane solution were shaken together for 10 minutes after which the two layers were separated. The lower dichloromethane layer exhibited λm ca 355 nm of 1.61 absorbance (corresponding to ca 36% ε uptake of silver picrate). The aqueous layer was at this point submitted for atomic absorption analysis to determine remaining Na and Ag levels. The dichloromethane layer was then treated for 5 minutes with 10% by weight Amberlyst A-21 (Trade Mark) ion-exchange resin (weakly basic, macroreticular resin available from Aldrich Chemical Co. Ltd.) which had been washed alternately twice with analar acetone and twice with HPLC grade dichloromethane (first filtered off). After this period of time the λm ca 355 nm of 1.61 absorbance was reduced to a shoulder of 0.08 absorbance as the solution became visually colourless. This same solution was then shaken with an equal volume of fresh sample of silver picrate/sodium picrate mixture ($2.5 \times 10^{-4}$M in both) for 10 minutes and the by now yellow coloured dichloromethane layer was again analysed by ultraviolet spectrometry. The absorbance at λm ca 355 nm was 1.53. The aqueous layer was submitted for analysis by atomic absorption for Na, Ag levels. As a control experiment dichloromethane was shaken alone with 10% by weight washed (as before) Amberlyst A-21 resin and subsequently (after filtering off the Amberlyst resin) shaken for 10 minutes with an equal volume of fresh sodium picrate/silver picrate solution. The absorbance at λm 355 nm of the dichloromethane layer was measured spectrophotometrically to be nil. The aqueous layer was submitted for Na and Ag determination by atomic absorption analysis. The spectrophotometric evidence indicates take up and release of metal picrate. The atomic absorption results indicating Na, Ag levels are given below:

| Aqueous Sample of Sodium/Silver Picrate | Na ppm | Ag ppm |
|---|---|---|
| Before treatment | 6 | 25 |
| After treatment with solution of Compound of Example 1 | 5 | 16(64%) |
| After treatment with above Calixarene Solution Treated with washed Amberlyst A-21 | 9 | 10(40%) |
| After treatment with Dichloromethane Treated with washed Amberlyst A-21 | 7 | 23 |

These results confirm those results obtained spectrophotometrically which together show that the compound of Example 1 specifically sequesters silver from a silver picrate/sodium picrate aqueous mixture (36% determined independently by U-V and atomic absorption analysis) and can then be made to release it by use of Amberlyst A-21 resin and still be found subsequently to be effective at specifically sequestering silver again from a silver picrate/sodium picrate mixture.

This experiment was repeated employing $8.3 \times 10^{-5}$M dichloromethane solution of the compound of Example 4 which was shaken with an equal volume of fresh sodium picrate, silver picrate solution $2.5 \times 10^{-4}$M for 10 minutes. After this time the dichloromethane layer had λm 355 of 1.36 absorbance corresponding to % ε silver picrate 30.3%. This layer after having been treated with 10% by weight prewashed Amberlyst A-21 resin exhibited λm 355 of zero. This dichloromethane solution was subsequently shaken with a fresh silver picrate/sodium picrate solution for 10 minutes and its absorbance at λm 355 nm found to be 0.89 corresponding to % ε silver picrate 19.9% ε. Thus the present inventor demonstrated again the ability of a nitrogen-containing calixarene derivative to target in on a silver picrate/sodium picrate solution and sequester silver alone, then be made to release it and subsequently to be reused to sequester silver from a fresh silver picrate/sodium picrate mixture.

What is claimed is:

1. Nitrogen-containing calixarene derivatives selected from the group represented by the forumlae:

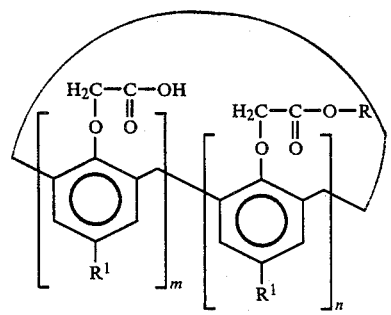

and

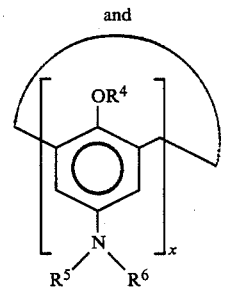

wherein
m+n=4, 6, or 8
n=an integer 1–8
m=an integer 0–7
x=4, 6 or 8
$R^1$ is H, alkyl, aralkyl, alkoxy, aroyl, or alkoyl,
R is aliphatic or aromatic, unsubstituted or substitied hydrocarbyl containing nitrogen,
$R^4$ is unsubstituted or substituted hydrocarbyl, carbonyl or aryl;
$R^5$ and $R^6$ (which may be the same or different) are hydrogen, or unsubstituted or substituted hydrocarbyl.

2. Calixarene derivatives of formula I according to claim 1, wherein the radical R contains an amino or amido group.

3. Calixarene derivatives according to claim 2, wherein R is a group of the formula

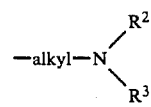

where $R^2$ and $R^3$ represent H or substituted or unsubstituted hydrocarbyl.

4. Calixarene derivatives of formula I according to claim 1, wherein the radical R contains a heterocyclic ring which may be saturated or unsaturated, aliphatic or aromatic.

5. Calixarene derivatives according to claim 4, wherein R is a 5- or 6-membered ring containing one or more nitrogen atoms or a fused ring compound containing one or more nitrogen atoms.

6. Calixarene derivatives of formula I according to claim 1, wherein R is an aromatic compound of the formula

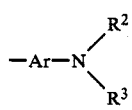  V wherein $R^2$ and $R^3$ are as defined in claim 3.

7. Calixarene derivatives of formula I according to claim 1, wherein R is an azo compound of the formula

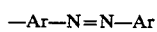  VI where Ar represents an aromatic radical.

8. Calixarene derivatives of formula I according to claim 1 selected from

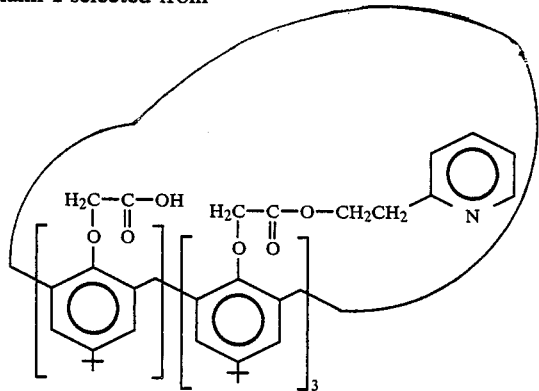

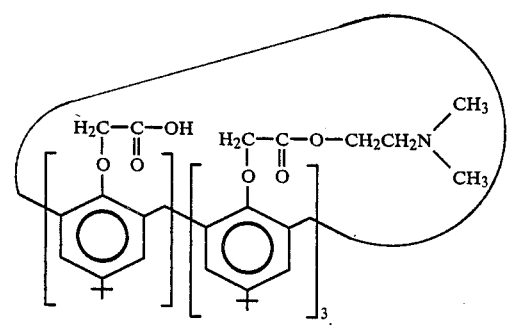

-continued

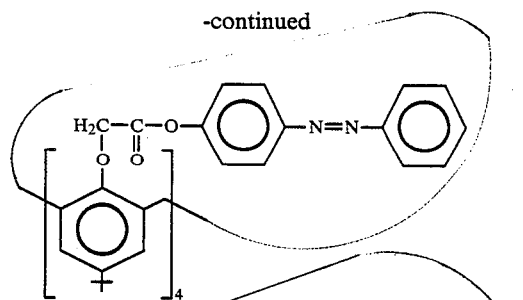

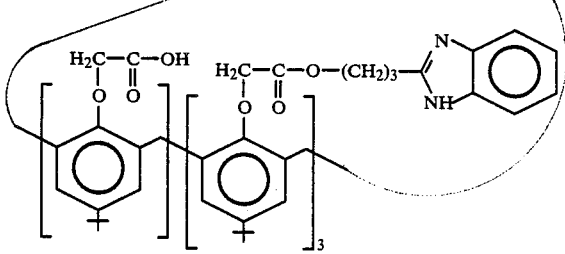

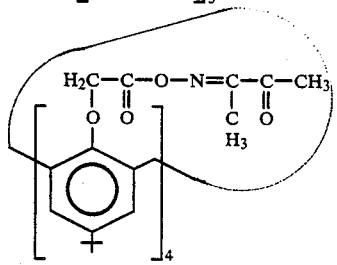

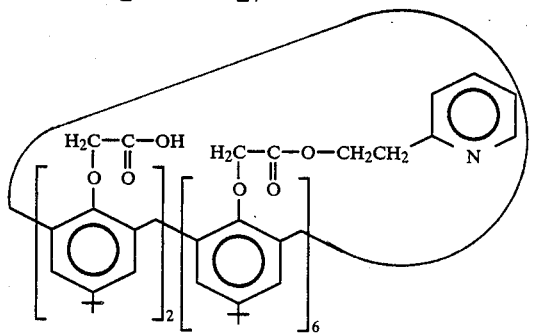

9. Calixarene derivatives of formula II according to claim 1 wherein $R^4$ is alkyl or alkenyl having 1-5 carbon atoms.

10. Calixarene derivatives of formula II according to claim 1 wherein $R^5$ and $R^6$ are hydrogen.

11. Calixarene derivative of formula II according to claim 1 which is the allyl ether of p-Aminocalix-4-arene having the formula

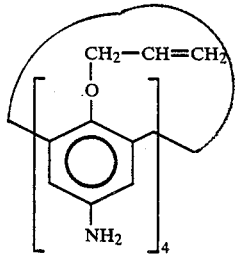

* * * * *